United States Patent
Ysebaert et al.

(10) Patent No.: US 11,369,612 B2
(45) Date of Patent: Jun. 28, 2022

(54) TREATMENT OF RSV WITH COMBINATION PRODUCT

(71) Applicant: Janssen Sciences Ireland Unlimited Company, County Cork (IE)

(72) Inventors: Nina Ysebaert, Brasschaat (BE); Nele Isa E. Goeyvaerts, Kuringen (BE); Dirk André Emmy Roymans, Turnhout (BE); Anil Koul, Edegem (BE)

(73) Assignee: Janssen Sciences Ireland Unlimited Company, County Cork (IE)

( * ) Notice: Subject to any disclaimer, the term of this patent is extended or adjusted under 35 U.S.C. 154(b) by 10 days.

(21) Appl. No.: 16/770,014

(22) PCT Filed: Dec. 4, 2018

(86) PCT No.: PCT/EP2018/083440
§ 371 (c)(1),
(2) Date: Jun. 4, 2020

(87) PCT Pub. No.: WO2019/110563
PCT Pub. Date: Jun. 13, 2019

(65) Prior Publication Data
US 2021/0236496 A1 Aug. 5, 2021

(30) Foreign Application Priority Data
Dec. 5, 2017 (EP) .................................... 17205428

(51) Int. Cl.
*A61K 31/519* (2006.01)
*A61K 31/44* (2006.01)
*A61P 31/14* (2006.01)
*A61K 31/437* (2006.01)

(52) U.S. Cl.
CPC .......... *A61K 31/519* (2013.01); *A61K 31/437* (2013.01); *A61P 31/14* (2018.01)

(58) Field of Classification Search
CPC ...... A61K 31/437; A61K 31/519; A61P 31/14
USPC .............................................. 514/259.3, 303
See application file for complete search history.

(56) References Cited

U.S. PATENT DOCUMENTS 10,611,769 B2 * 4/2020 Lancois ............... A61K 31/437

FOREIGN PATENT DOCUMENTS

| WO | 2012/080447 | 6/2012 |
| WO | 2016/174079 A1 | 11/2016 |
| WO | 2017134133 | 8/2017 |

OTHER PUBLICATIONS

Jong et al. "Consensus symposium on combined antiviral therapy," Antiviral Research, 1995, vol. 29, pp. 5-29 (Year: 1995).*
Hallack, et al., "Glycosaminoglycan Sulfation Requirements for Respiratory Syncytial Virus Infection," Journal of Virology, vol. 74(22):pp. 10508-10513 (Nov. 2000).
Harbron, "A flexible unified approach to the analysis of pre-clinical combination studies", Statistics in Medicine, vol. 29; pp. 1746-1756 (Apr. 6, 2010).
Huntjens, et al, "Population Pharmacokinetic Modeling of JNJ-53718678, a Novel Fusion Inhibitor for the Treatment of Respiratory Syncytial Virus: Results from a Phase I, Double-Blind, Randomized, Placebo-Controlled First-in-Human Study in Healthy Adult Subjects", Clinical Pharmacokinetics, vol. 56 (11); pp. 1331-1342 (Oct. 31, 2017).
Roymans, et al, "Therapeutic efficacy of a respiratory syncytial virus fusion inhibitor," Nature Communications, vol. 8(1), Article 167 (Aug. 1, 2017).
International Search Report and Written Opinion for PCT Patent Application No. PCT/EP2018/083440 dated Mar. 6, 2019.

* cited by examiner

*Primary Examiner* — Shengjun Wang

(57) ABSTRACT

The present invention is directed to the combination of the RSV inhibiting Compound A, i.e. 3-({5-chloro-1-[3-(methylsulfonyl)propyl]-1H-indol-2-yl}methyl)-1-(2,2,2-trifluoroethyl)-1,3-dihydro-2H-imidazo[4,5-c]pyridin-2-one, and the RSV inhibiting Compound B, i.e. (1S,2S)-2-[4-[7-cyclopropyl-5-[(1R)-1-methyl-3,4-dihydro-1H-isoquinoline-2-carbonyl]pyrazolo[1,5-a]pyrimidin-2-yl]-3-fluoro-phenyl]cyclopropanecarboxylic acid for treating or ameliorating RSV infection. The invention further relates to the combination product of Compound A and Compound B, a pharmaceutical product comprising Compound A and Compound B, the use of the combination of Compound A and Compound B—or the pharmaceutical product comprising Compound A and Compound B—for the treatment of RSV infection, and a method of treating or ameliorating RSV infection in a subject in need thereof comprising administering the combination of Compound A and Compound B in an effective amount to said subject.

17 Claims, No Drawings

TREATMENT OF RSV WITH COMBINATION PRODUCT

CROSS-REFERENCE TO RELATED APPLICATIONS

This application is a national phase entry of International Application No. PCT/EP2018/083440, filed on Dec. 4, 2018, which claims priority to EP Patent Application No. 17205428.0, filed Dec. 5, 2017, each of which is incorporated herein in its entirety.

The present invention is directed to the combination of the RSV inhibiting Compound A, i.e. 3-({5-chloro-1-[3-(methylsulfonyl)propyl]-1H-indol-2-yl}methyl)-1-(2,2,2-trifluoroethyl)-1,3-dihydro-2H-imidazo[4,5-c]pyridin-2-one, and the RSV inhibiting Compound B, i.e. (1S,2S)-2-[4-[7-cyclopropyl-5-[(1R)-1-methyl-3,4-dihydro-1H-isoquinoline-2-carbonyl]pyrazolo[1,5-a]pyrimidin-2-yl]-3-fluoro-phenyl]cyclopropanecarboxylic acid for treating or ameliorating RSV infection. The invention further relates to the combination product of Compound A and Compound B, a pharmaceutical product comprising Compound A and Compound B, the use of the combination of Compound A and Compound B—or the pharmaceutical product comprising Compound A and Compound B—for the treatment of RSV infection, and a method of treating or ameliorating RSV infection in a subject in need thereof comprising administering the combination of Compound A and Compound B in an effective amount to said subject.

Human RSV or Respiratory Syncytial Virus is a large RNA virus—member of the family of Pneumoviridae, genus *Orthopneumovirus*—together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Today only three drugs have been approved for use against RSV infection. A first one is ribavirin, a nucleoside analogue that provides an aerosol treatment for serious RSV infection in hospitalized children. The other two drugs, RespiGam® (RSV-IG) and Synagis® (palivizumab), polyclonal and monoclonal antibody immunostimulants, are intended to be used in a preventive way. Both are very expensive, and require parenteral administration.

Compound A, i.e. 3-({5-chloro-1-[3-(methylsulfonyl)-propyl]-1H-indol-2-yl}methyl)-1-(2,2,2-trifluoroethyl)-1,3-dihydro-2H-imidazo[4,5-c]pyridin-2-one, is disclosed in WO-2012/080447 as compound P55.

Compound B, i.e. (1S,2S)-2-[4-[7-cyclopropyl-5-[(1R)-1-methyl-3,4-dihydro-1H-isoquinoline-2-carbonyl]pyrazolo[1,5-a]pyrimidin-2-yl]-3-fluoro-phenyl]cyclopropanecarboxylic acid, is disclosed in WO-2016/174079 as compound O5.

WO-2017/134133 discloses combinations of 3-({5-chloro-1-[3-(methylsulfonyl)-propyl]-1H-indol-2-yl}methyl)-1-(2,2,2-trifluoroethyl)-1,3-dihydro-2H-imidazo[4,5-c]pyridin-2-one, and one or more RSV inhibiting compounds for use in the treatment of RSV infection.

It has now been found that the combination of 3-({5-chloro-1-[3-(methylsulfonyl)-propyl]-1H-indol-2-yl}methyl)-1-(2,2,2-trifluoroethyl)-1,3-dihydro-2H-imidazo[4,5-c]pyridin-2-one (hereinafter referred to as Compound A) and (1S,2S)-2-[4-[7-cyclopropyl-5-[(1R)-1-methyl-3,4-dihydro-1H-isoquinoline-2-carbonyl]pyrazolo[1,5-a]pyrimidin-2-yl]-3-fluoro-phenyl]cyclopropanecarboxylic acid (hereinafter referred to as Compound B), provides an improved therapy in the treatment of RSV infection.

Some embodiments disclosed herein relate to the combination of Compound A and Compound B and the use of this combination for preventing, treating or ameliorating RSV infection in a subject in need thereof.

Other embodiments relate to a pharmaceutical product comprising the combination of Compound A and Compound B and the use of said pharmaceutical product for preventing, treating or ameliorating RSV infection.

Still other embodiments relate to a method of preventing, treating or ameliorating RSV infection in a subject in need thereof comprising administering the combination of Compound A and Compound B in an effective amount to said subject.

Compound A is 3-({5-chloro-1-[3-(methylsulfonyl)propyl]-1H-indol-2-yl}methyl)-1-(2,2,2-trifluoroethyl)-1,3-dihydro-2H-imidazo[4,5-c]pyridin-2-one disclosed in WO-2012/080447 as compound P55 having the following structure:

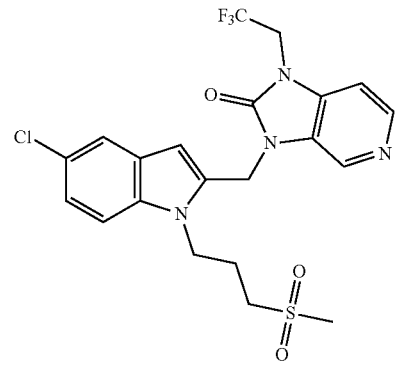 [SMILES: CS(=O)(=O)CCCn1c(Cn2c(=O)n(CC(F)(F)F)c3ccncc32)cc2cc(Cl)ccc21]

Compound B is (1S,2S)-2-[4-[7-cyclopropyl-5-[(1R)-1-methyl-3,4-dihydro-1H-isoquinoline-2-carbonyl]pyrazolo[1,5-a]pyrimidin-2-yl]-3-fluoro-phenyl]cyclopropanecarboxylic acid disclosed in WO-2016/174079 as compound O5 having the following structure (single stereoisomer with relative stereochemistry for the cyclopropyl moiety):

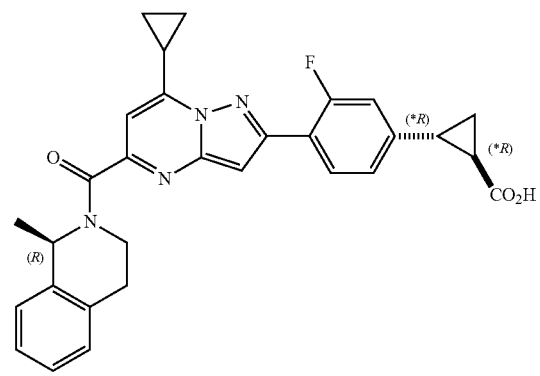

which has been later found to have the following absolute stereochemistry:

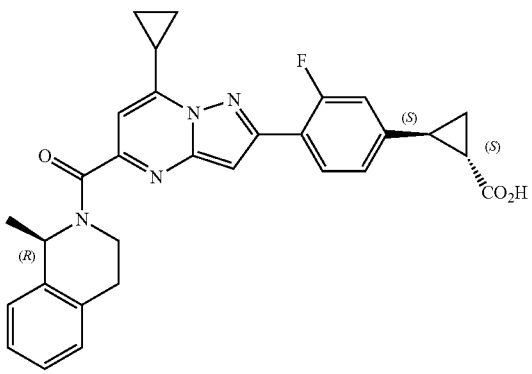

Whenever used hereinafter the term Compound A or Compound B it is meant to include both the Compound A and/or Compound B in its free base form and the pharmaceutically acceptable salt forms thereof.

The Compound A or Compound B may be used in pharmaceutically acceptable salt forms or in free (i.e. non-salt) form. Salt forms can be obtained by treating the free form with an acid or base. Of interest are the pharmaceutically acceptable acid and base addition salts, which are meant to comprise the therapeutically active non-toxic acid and base addition salt forms that the compounds are able to form. The pharmaceutically acceptable acid addition salts of the Compound A or Compound B can conveniently be obtained by treating the free form with such appropriate acid. Appropriate acids comprise, for example, inorganic acids such as hydrohalic acids, such as hydrobromic acid, or in particular hydrochloric acid; or sulfuric, nitric, phosphoric and the like acids; or organic acids such as, for example, acetic, propanoic, hydroxyacetic, lactic, pyruvic, oxalic, malonic, succinic, maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. The Compound A or Compound B may also be converted into the pharmaceutically acceptable metal or amine addition salt forms by treatment with appropriate organic or inorganic bases. Appropriate base salt forms comprise, for example, the ammonium salts, the alkali and earth alkaline metal salts, e.g. the lithium, sodium or potassium salts; or the magnesium or calcium salts; salts with organic bases, e.g. the benzathine, N-methyl-D-glucamine, hydrabamine salts, and salts with amino acids such as, for example, arginine, lysine, and the like. The term addition salt form is meant to also comprise any solvates that Compound A or Compound B, as well as the salts thereof, may form. Such solvates are, for example, hydrates, alcoholates, e.g. ethanolates, and the like.

In an embodiment the amount of Compound A and the amount of Compound B in the combinations according to the present invention is such that a synergistic antiviral effect against RSV is obtained.

The amounts of the Compound A in the combinations of the invention that are administered on a daily basis may vary from about 10 mg to about 2500 mg, about 50 mg to about 1000 mg, or from about 50 mg to about 500 mg.

The amounts of the Compound B in the combinations of the invention that are administered on a daily basis may vary from about 10 mg to about 2500 mg, about 50 mg to about 1000 mg, or from about 50 mg to about 500 mg for the total amount of the Compound B.

All amounts mentioned in this and the following paragraphs refer to the free form (i.e. non-salt form). The above values represent free-form equivalents, i.e. quantities as if the free form would be administered. If salts are administered the amounts need to be calculated in function of the molecular weight ratio between the salt and the free form. The above mentioned daily doses are calculated for an average body weight of about 70 kg and should be recalculated in case of paediatric applications, or when used with patients with a substantially diverting body weight.

The dosages may be presented as one, two, three or four or more sub-doses administered at appropriate intervals throughout the day. The dosage used preferably corresponds to the daily amount of Compound A and Compound B mentioned above, or a sub-dose thereof, such as ½, ⅓, or ¼ thereof. A dosage form may contain the Compound A and Compound B, in an amount equal to the ranges or quantities mentioned in the previous paragraphs, either in separate formulations or in a combined formulation. Such combined formulation is preferred.

In the instance where Compound A and Compound B are to be administered once daily, this can be accomplished by administering a combined fixed dose combination containing Compound A and Compound B. Dosage forms that can be administered are described hereinafter, oral dosage forms, in particular oral solutions being preferred.

Active ingredients may be formulated in pharmaceutical compositions either separately or as a combined pharmaceutical composition. In the latter instance, there is provided a pharmaceutical composition comprising a therapeutically effective amount of Compound A, or a pharmaceutically acceptable salt thereof, and the Compound B, or a pharmaceutically acceptable salt thereof, and a pharmaceutically acceptable carrier. A therapeutically effective amount in this context is an amount sufficient to stabilize or to reduce RSV infection, in infected subjects. Therapeutically effective amounts may in particular correspond to the amounts mentioned above for administration on a daily base or of the subdoses thereof in ease of multiple daily administrations.

In a further aspect, this invention relates to a process of preparing a pharmaceutical composition as specified herein, which comprises intimately mixing a pharmaceutically acceptable carrier with a therapeutically effective amount of the Compound A, or a pharmaceutically acceptable salt thereof, and an effective amount of the Compound B, or a pharmaceutically acceptable salt thereof.

The combinations provided herein may also be formulated as a combined preparation for simultaneous or sequential use in RSV therapy. In such a case, the Compound A is formulated in a pharmaceutical composition containing other pharmaceutically acceptable excipients, and the Compound B is formulated separately in a pharmaceutical composition containing other pharmaceutically acceptable excipients.

Conveniently, these separate pharmaceutical compositions can be part of a kit for simultaneous or sequential use.

The individual components of the combination of the present invention can be administered simultaneously or separately at different times during the course of therapy or concurrently in divided or single combination forms.

Therefore, the Compound A and Compound B, individually or combined, may be formulated into various pharmaceutical compositions suitable for administration purposes. In these, a therapeutically effective amount of each of the particular compounds A and B is combined with a pharmaceutically acceptable carrier, which carrier may take a wide variety of forms depending on the form of preparation desired for administration. Pharmaceutical compositions may be prepared as medicaments to be administered orally, parenterally (including subcutaneously, intramuscularly, and intravenously), rectally, bucally, or nasally. Suitable compositions for oral administration include powders, granulates, aggregates, tablets, compressed or coated pills, dragees, sachets, hard or gelatin capsules, syrups and suspensions. Suitable compositions for parenteral administration include aqueous or non-aqueous solutions or emulsions, while for rectal administration suitable compositions for administration include suppositories with a hydrophilic or hydrophobic vehicle. For nasal delivery there can be used suitable aerosol delivery systems.

For example, in preparing the compositions for oral administration, any of the usual pharmaceutical media may be employed such as, for example, water, glycols, oils, alcohols and the like in the case of oral liquid compositions such as suspensions, syrups, elixirs, emulsions and solutions; or solid carriers such as starches, sugars, kaolin, lubricants, binders, disintegrating agents and the like in the case of solid compositions. For parenteral compositions, the carrier will usually comprise sterile water, at least in large part, though other ingredients, such as solubilizers, emulsifiers or further auxiliaries may be added thereto. Injectable solutions may be prepared in which the carrier comprises saline solution, glucose solution or a mixture of both. Injectable suspensions may also be prepared in which case appropriate liquid carriers, suspending agents and the like may be employed. Also included are solid form preparations intended to be converted, shortly before use, to liquid form preparations such as powders for reconstitution.

The pharmaceutical compositions may be conveniently presented in unit dosage form for ease of administration and uniformity of dosage. Examples include tablets (including scored or coated tablets), capsules, pills, suppositories, powder packets, wafers, injectable solutions or suspensions and the like, and segregated multiples thereof.

The combination of Compound A and Compound B, as specified herein, is useful in the treatment of warm-blooded animals, in particular humans, infected with RSV.

The present invention also relates to a method for treating or ameliorating RSV infection in a subject in need thereof comprising administering the combination of Compound A and Compound B, or a pharmaceutically acceptable salt of any of the foregoing, in a therapeutically effective amount to said subject. The amount of Compound A can range from 1 mg/kg to 50 mg/kg or 5 mg/kg to 50 mg/kg and the amount of Compound B can range from 1 mg/kg to 50 mg/kg or 5 mg/kg to 50 mg/kg.

In an embodiment the present invention further relates to a method for treating or ameliorating RSV infection in a subject in need thereof comprising administering the combination of Compound A and Compound B, or a pharmaceutically acceptable salt of any of the foregoing, wherein the amount of Compound A and the amount of Compound is such that a synergistic antiviral effect against RSV is obtained.

Other embodiments relate to a method for treating or ameliorating a RSV infection comprising contacting a cell infected with the RSV virus with an effective amount of a combination of Compound A and of Compound B, or a pharmaceutically acceptable salt of any of the foregoing.

As used herein, the terms "treat," "treating," "treatment," "therapeutic," and "therapy" do not necessarily mean total cure or abolition of the disease or condition. Any reduction of viral load or alleviation of any undesired signs or symptoms of a disease or condition, to any extent can be considered treatment and/or therapy.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, alleviate or ameliorate symptoms of disease, reduce viral load, or prolong the survival of the subject being treated. This response may occur in a tissue, system, animal or human and includes reduction of viral load, alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

Various indicators for determining the effectiveness of a method for treating a respiratory syncytial virus (RSV) infection are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator of disease response.

In some embodiments, a combination of Compound A and of Compound B, or a pharmaceutical acceptable salt of the foregoing, can reduce viral titers to undetectable levels, for example, less than 1.7 $\log_{10}$ plaque forming units equivalents (PFUe)/mL, or less than 0.3 $\log_{10}$ plaque forming units equivalents (PFUe)/mL. In some embodiments, a combination of compounds described herein can reduce the viral load compared to the viral load before administration of the combination (for example, 60 hours after receiving the initial dosage of the combination). In some embodiments, a combination of compounds described herein can reduce the viral load to lower than 1.7 $\log_{10}$ (PFUe)/mL, or lower than 0.3 $\log_{10}$ (PFUe)/mL. In some embodiments, a combination of compounds described herein can achieve a reduction in viral titer in the serum of the subject in the range of about 1.5-log to about a 2.5-log reduction, about a 3-log to about a 4-log reduction, or a greater than about 5-log reduction compared to the viral load before administration of the combination. For example, the viral load is measure before administration of the combination, and several hours after receiving the initial dosage of the combination (for example, 60 hours after receiving the initial dosage of the combination).

In some embodiments, a combination of Compound A and of Compound B, or a pharmaceutical acceptable salt of the foregoing, can result in at least a 1, 2, 3, 4, 5, 10, 15, 20, 25, 50, 75, 100-fold or more reduction in the replication of RSV relative to pre-treatment levels in a subject, as determined several hours after receiving the initial dosage of the combination (for example, 60 hours after receiving the initial dosage of the combination). In some embodiments, a combination as described herein can result in a reduction of the replication of RSV relative to pre-treatment levels in the range of about 2 to about 5 fold, about 10 to about 20 fold, about 15 to about 40 fold, or about 50 to about 100 fold. In some embodiments, a combination as described herein can result in a reduction of RSV replication in the range of 1 to 1.5 log, 1.5 log to 2 log, 2 log to 2.5 log, 2.5 to 3 log, 3 log to 3.5 log or 3.5 to 4 log more reduction of RSV replication compared to the reduction of RSV reduction achieved by the use of one anti-RSV agent administered as monotherapy, or may achieve the same reduction in a shorter period of time.

After a period of time, infectious agents can develop resistance to therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a combination of Compound A and Compound B, or a pharmaceutical acceptable salt of the foregoing, can be administered to a subject infected with RSV that is resistant to different anti-RSV agents (for example, ribavirin). In some embodiments, development of resistant RSV strains can be delayed when subjects are treated with combination of compounds described herein compared to the development of RSV strains resistant to other anti-RSV agents administered as monotherapy.

In some embodiments, a combination of Compound A and Compound B, or a pharmaceutical acceptable salt of the foregoing, can decrease the percentage of subjects that experience complications from a RSV viral infection compared to the percentage of subjects that experience complication being treated with one anti-RSV agent. For example, the percentage of subjects being treated with a combination of compounds described herein that experience complications can be 5%, 10%, 25%, 40%, 50%, 60%, 70%, 80% and 90% less compared to subjects being treated with only one anti-RSV agent administered as monotherapy.

A potential advantage of utilizing a combination of Compound A and of Compound B, or a pharmaceutical acceptable salt of the foregoing, may be a reduction in the required amount(s) of Compound A, or a pharmaceutically acceptable salt thereof, and/or of Compound B, or a pharmaceutically acceptable salt thereof, that is effective in treating RSV infection, as compared to the amount required to achieve same therapeutic result when of Compound (B), or a pharmaceutically acceptable salt thereof, and/or Compound A, or a pharmaceutically acceptable salt thereof. For example, the amount of Compound A, or a pharmaceutically acceptable salt thereof, and/or of Compound B, or a pharmaceutically acceptable salt thereof, can be less compared to the amount of the aforementioned compounds needed to achieve the same viral load reduction when administered as a monotherapy. Another potential advantage of utilizing a combination described herein is that the use of two or more compounds having different mechanism of actions can create a higher barrier to the development of resistant viral strains compared to the barrier when a compound is administered as monotherapy. Additional advantages of utilizing a combination described herein may include little to no cross resistance between the compounds of the combination; different routes for elimination of the compounds of the combination; little to no overlapping toxicities between the compounds of the combination; little to no significant effects on cytochrome P450; and/or little to no pharmacokinetic interactions between the compounds of the combination.

EXAMPLES

The following examples are intended to illustrate the present invention and not to limit it thereto.

Example 1: RSV Assay Combination Experiments

To evaluate their combined antiviral effect against RSV, in vitro combination studies were performed with Compound A, i.e. 3-({5-chloro-1-[3-(methylsulfonyl)propyl]-1H-indol-2-yl}methyl)-1-(2,2,2-trifluoroethyl)-1,3-dihydro-2H-imidazo[4,5-c]pyridin-2-one, and Compound B, i.e. (1S,2S)-2-[4-[7-cyclopropyl-5-[(1R)-1-methyl-3,4-dihydro-1H-isoquinoline-2-carbonyl]pyrazolo[1,5-a]pyrimidin-2-yl]-3-fluoro-phenyl]cyclopropanecarboxylic acid. In short, 9 concentrations of Compound A were combined with 6 or 7 concentrations of Compound B. HeLa cells were infected with rgRSV224, an engineered RSV strain that encodes for eGFP (Hallak L K, Spillmann D, Collins P L, Peeples M E. Glycosaminoglycan sulfation requirements for respiratory syncytial virus infection; Journal of Virology (2000), 74(22), 10508-13), in the presence of various concentrations of compound A and compound B individually or in combination.

Compound stock solutions were 5 mM in 100% DMSO. First, the compounds were serially diluted in 3-fold dilution series in DMSO. The concentration series were diluted 100-fold in cell culture medium to achieve a combination matrix. 10 µL of these compound solutions were transferred to black 384-well clear-bottom tissue-culture treated plates. Next, 10 µL of a 150000 cells per mL HeLa cell suspension was added to achieve 3000 cells per well. Finally, 10 µL of diluted virus stock was added to achieve an MOI of 1. The final DMSO concentration of all wells was 0.5% DMSO. Each combination of compound concentrations was tested in 4 replicates on 3 separate plates, resulting in a total of 12 replicates. The plates were incubated for 3 days at 37° C. in a humidified atmosphere at 5% CO2. The GFP signal was measured with PerkinElmer EnVision apparatus using a 405 nm filter.

For the statistical analysis, the observed GFP signal was normalized using the virus controls (VC) and cell controls (CC) on the corresponding plate: response=(GFP−CC)/(VC−CC), where CC was computed as the median GFP for all blanc wells (no virus) and VC was computed as the median GFP for all control wells (no compound).

The method of Harbron (Statistics in Medicine, 2010, DOI:10.1002/sim3916) was used to assess synergy. Using the Loewe definition, two compounds are characterized as being additive, synergistic or antagonistic by:

$$\frac{d_1}{D_{y,1}} + \frac{d_2}{D_{y,2}} \begin{cases} = 1, & \text{additivity} \\ < 1, & \text{synergy} \\ > 1, & \text{antagonism} \end{cases}$$

where $d_1$ and $d_2$ represent the doses of the two compounds that in combination produce an effect y, and $D_{y,1}$ and $D_{y,2}$ represent the doses of the two compounds that produce the same effect, y, when administered as a monotherapy. A 3PL model (3-parameter log-logistic model) was used for the monotherapy dose-response data, where the baseline response was fixed at one.

Following Harbron's approach, the following models were fitted to the data:

"Additive": assuming no interaction between the two compounds

"Uniform": assuming a constant interaction index τ across all dose combinations

"Linear A": assuming the interaction index linearly depends on the log 10 dose of compound A: $\tau=\tau_1+\tau_2 \log 10(d_A)$ "Separate A": assuming the interaction index τ takes a separate value for each dose of compound A The latter two models were also considered for compound B:

"Linear B": assuming the interaction index linearly τ depends on the log 10 dose of compound B: $\tau=\tau_1+\tau_2 \log 10(d_B)$ "Separate B": assuming the interaction index τ takes a separate value for each dose of compound B The "Separate A" model was selected for all tested combinations based on Akaike's Information Criterion (AIC). The test results for the combinations of Compound A with Compound B are reported below.

Combination: Compound A and Compound B

TABLE 1 normalized data for Compound A in combination with Compound B (average across 12 replicates).

|  | A = 0 | A = 0.19 | A = 0.57 | A = 1.7 | A = 5.1 | A = 15 | A = 46 | A = 139 | A = 417 | A = 1250 |
|---|---|---|---|---|---|---|---|---|---|---|
| B = 0 | 1.09 | 1.07 | 1.05 | 0.99 | 0.74 | 0.48 | 0.29 | 0.18 | 0.08 | 0.06 |
| B = 4.6 | 1.13 | 1.10 | 1.04 | 0.92 | 0.59 | 0.35 | 0.18 | 0.11 | 0.06 | 0.03 |
| B = 14 | 1.04 | 1.01 | 0.90 | 0.65 | 0.36 | 0.18 | 0.10 | 0.06 | 0.03 | 0.02 |
| B = 42 | 0.37 | 0.32 | 0.24 | 0.15 | 0.07 | 0.03 | 0.02 | 0.01 | 0.00 | 0.01 |
| B = 125 | 0.07 | 0.05 | 0.04 | 0.02 | 0.00 | −0.01 | −0.01 | 0.00 | 0.00 | 0.00 |
| B = 375 | 0.00 | 0.00 | 0.00 | −0.01 | −0.01 | −0.01 | −0.01 | 0.00 | 0.00 | 0.00 |
| B = 1125 | 0.00 | 0.00 | 0.01 | 0.00 | 0.00 | −0.01 | 0.00 | 0.01 | 0.00 | 0.00 |

Table 2 shows the interaction index (τ) estimates with 95% confidence intervals (CIs) for the "separate A" model. Allowing the degree of synergy to vary by doses of Compound A, reveals a significant degree of synergy for doses of 0.57 nM and higher. Overall, the degree of synergy increases with increasing dose levels.

TABLE 2 estimated values for interaction indicates with 95% CIs for 'separate A' model. The interaction index at the EC50 value is approximated by linear interpolation of the tau estimates.

|  | Dose (nM) | Estimate | 95% CI |
|---|---|---|---|
| $\tau_1$ | 0.19 | 0.975 | (0.933, 1.019) |
| $\tau_2$ | 0.57 | 0.876 | (0.834, 0.921) |
| $\tau_3$ | 1.7 | 0.686 | (0.648, 0.726) |
| $\tau_4$ | 5.1 | 0.543 | (0.51, 0.577) |
| $\tau_5$ | 15 | 0.543 | (0.494, 0.598) |
| $\tau_6$ | 46 | 0.483 | (0.392, 0.595) |
| $\tau_7$ | 139 | 0.342 | (0.133, 0.875) |
| $\tau_8$ | 417 | 0.158 | (0.116, 0.214) |
| $\tau_9$ | 1250 | 0.054 | (0.042, 0.07) |
| τ EC 50 | 13.09 | 0.543 | (NA, NA) |

Example 2: In Vivo RSV Combination Experiments

The combination of Compound A and Compound B has also been studied in an in vivo neonatal lamb model. At the time of filing the patent application, the statistical analysis of the experiments was still ongoing but preliminary results support the in vitro synergy findings.

The invention claimed is:

1. A combination comprising:
   3-({5-chloro-1-[3-(methylsulfonyl)propyl]-1H-indol-2-yl}methyl)-1-(2,2,2-trifluoroethyl)-1,3-dihydro-2H-imidazo[4,5-c]pyridin-2-one, or a pharmaceutically acceptable salt thereof, as Compound A, and
   (1S,2S)-2-[4-[7-cyclopropyl-5-[(1R)-1-methyl-3,4-dihydro-1H-isoquinoline-2-carbonyl]-pyrazolo[1,5-a]pyrimidin-2-yl]-3-fluoro-phenyl]cyclopropanecarboxylic acid, or a pharmaceutically acceptable salt thereof, as Compound B,
   wherein the amounts of Compound A and Compound B are such that they produce a synergistic antiviral effect against RSV.

2. The combination of claim 1, wherein the amount of Compound A ranges from about 50 mg to about 500 mg in free form equivalent and the amount of Compound B ranges from about 50 mg to about 500 mg in free form equivalent.

3. A pharmaceutical composition comprising the combination of claim 1 and a pharmaceutically acceptable carrier.

4. The pharmaceutical composition of claim 3, wherein the amount of Compound A ranges from about 50 mg to about 500 mg in free form equivalent and the amount of Compound B ranges from about 50 mg to about 500 mg in free form equivalent.

5. The pharmaceutical composition of claim 3, wherein the composition is an oral pharmaceutical composition.

6. The pharmaceutical composition of claim 5, wherein the oral pharmaceutical composition is a tablet, a capsule, a solution, or a suspension.

7. The pharmaceutical composition of claim 3, wherein Compound A and Compound B are formulated in a single pharmaceutical composition.

8. A method for treating or ameliorating respiratory syncytial virus (RSV) infection in a subject in need thereof comprising administering to the subject the combination of claim 1.

9. The method of claim 8, wherein Compound A and Compound B are formulated in a single pharmaceutical composition.

10. The method of claim 8, wherein Compound A is formulated as a first separate pharmaceutical composition and Compound B is formulated as a second separate pharmaceutical composition, and the administering comprises administering the first and second separate pharmaceutical compositions to the subject simultaneously or sequentially.

11. The method of claim 8, wherein the amount of Compound A ranges from about 50 mg to about 500 mg in free form equivalent and the amount of Compound B ranges from about 50 mg to about 500 mg in free form equivalent.

12. The method of claim 9, wherein the single pharmaceutical composition is an oral pharmaceutical composition.

13. The method of claim 12, wherein the oral pharmaceutical composition is a tablet, a capsule, a solution, or a suspension.

14. The method of claim 10, wherein the first and second separate pharmaceutical compositions are each independently a tablet, a capsule, a solution, or a suspension.

15. The method of claim 8, comprising administering each of Compound A and Compound B daily to the subject in one, two, three, or four sub-doses at appropriate intervals.

16. The method of claim 8, wherein Compound A is administered in an amount greater than or equal to a concentration of 0.57 nM or an equivalent thereof.

17. The method of claim 7, wherein Compound B is administered in an amount greater than or equal to a concentration of 14 nM or an equivalent thereof.

* * * * *